(12) United States Patent
Jackson et al.

(10) Patent No.: US 10,837,048 B2
(45) Date of Patent: Nov. 17, 2020

(54) FLUIDIC CARD FOR ANALYSIS OF BIOCHIPS

(71) Applicant: Randox Laboratories Ltd., Crumlin (GB)

(72) Inventors: Stuart Jackson, Crumlin (GB); Marin Crockard, Crumlin (GB); Stephen Peter Fitzgerald, Crumlin (GB); John Lamont, Crumlin (GB); Ivan McConnell, Crumlin (GB)

(73) Assignee: Randox Laboratories Ltd., Crumlin (GB)

( * ) Notice: Subject to any disclaimer, the term of this patent is extended or adjusted under 35 U.S.C. 154(b) by 6 days.

(21) Appl. No.: 15/769,030

(22) PCT Filed: Oct. 27, 2016

(86) PCT No.: PCT/GB2016/053341
§ 371 (c)(1),
(2) Date: Apr. 17, 2018

(87) PCT Pub. No.: WO2017/072513
PCT Pub. Date: May 4, 2017

(65) Prior Publication Data
US 2018/0327823 A1    Nov. 15, 2018

(30) Foreign Application Priority Data
Oct. 27, 2015 (GB) .................................. 1518993.9

(51) Int. Cl.
*C12Q 1/6837* (2018.01)
*B01L 3/00* (2006.01)

(52) U.S. Cl.
CPC ...... *C12Q 1/6837* (2013.01); *B01L 3/502707* (2013.01); *B01L 3/502715* (2013.01);
(Continued)

(58) Field of Classification Search
CPC ......... B01L 2200/025; B01L 3/502707; B01L 2300/044; B01L 2300/0609; B01L 9/527;
(Continued)

(56) References Cited

U.S. PATENT DOCUMENTS 6,399,394 B1    6/2002 Dahm et al.
2004/0037739 A1*  2/2004 McNeely ................ B01F 5/10
                                                    422/417
(Continued)

FOREIGN PATENT DOCUMENTS

WO    02/072264 A1    9/2002
WO    2008/002462 A2    1/2008
(Continued)

OTHER PUBLICATIONS

Faux, Katarina, International Preliminary Report on Patentability, European Patent Office, PCT/GB2016/053341, dated Feb. 5, 2018.

*Primary Examiner* — Betty J Forman
(74) *Attorney, Agent, or Firm* — Gavrilovich, Dodd & Lindsey LLP

(57) ABSTRACT

A fluidic card assembly comprising a fluidic card housing (1) and a biochip (3) located in the fluidic card housing. The fluidic card housing (1) includes a chamber (2) with a base wall, into which at least one fluidic channel extends. The biochip (3) is at least partially located in the chamber. A seal (7) is provided for sealing the biochip in the chamber (2) when the biochip is urged into the chamber. The fluidic channel has a serpentine form.

17 Claims, 6 Drawing Sheets

(52) U.S. Cl.
CPC . *B01L 2200/028* (2013.01); *B01L 2200/0689* (2013.01); *B01L 2200/141* (2013.01); *B01L 2300/0618* (2013.01); *B01L 2300/087* (2013.01); *B01L 2300/0816* (2013.01); *B01L 2300/0883* (2013.01); *B01L 2300/0887* (2013.01)

(58) Field of Classification Search
CPC ....... B01L 2200/028; B01L 2200/0689; B01L 2300/0618; B01L 2300/0816; B01L 2300/0887; C12Q 1/6837; G01N 1/28; B65D 71/50
See application file for complete search history.

(56) References Cited

U.S. PATENT DOCUMENTS

| | | |
|---|---|---|
| 2004/0086424 A1 | 5/2004 | Schembri et al. |
| 2010/0068822 A1* | 3/2010 | Heydenhauss ...... B01L 3/50273 436/172 |
| 2012/0164036 A1* | 6/2012 | Stern ................. B01L 3/502738 422/502 |
| 2012/0177543 A1* | 7/2012 | Battrell ............... B01F 11/0071 422/187 |
| 2013/0209326 A1 | 8/2013 | Williams et al. |

FOREIGN PATENT DOCUMENTS

| | | |
|---|---|---|
| WO | 2008/089769 A2 | 7/2008 |
| WO | 2013/192289 A1 | 12/2013 |

* cited by examiner

FLUIDIC CARD FOR ANALYSIS OF BIOCHIPS

CROSS REFERENCE TO RELATED APPLICATION

This application is a U.S. National Stage Application filed under 35 U.S.C. § 371 and claims priority to International Application No. PCT/GB2016/053341, filed Oct. 27, 2016, which application claims priority to Great Britain Application No. 1518993.9, filed Oct. 27, 2015, the disclosures of which are incorporated herein by reference in their entireties.

The present invention relates to improvements relating to the analysis of biochips. In particular, the present invention is directed to an improved assembly comprising a biochip. In another aspect of the invention there is provided an improved method for analysing a biochip. In a further aspect of the invention there is provided an improved biochip analyser for analysing a biochip.

Biochips comprise a reaction platform having at least one reaction zone, also known as a test region, to detect a specific analyte or biomarker. Multiple reaction zones may be present on the substrate allowing multiple different reactions to be performed simultaneously at each reaction zone. Such biochips provide an efficient screening method for diagnostic procedures, drug discovery and other research applications across a range of disciplines.

Conventionally, biochip assays are performed in the laboratory where biochips are housed in large open containers, known as fluid baths, for easy access to the biochip surface by pipette. The biochips are immersed in volumes of fluid running into 100s of microlitres, often millimetres of fluid, at various times in the assay protocol. Energy is required to heat and agitate the immersed biochip to accelerate the reactions of the fluid with each test region on the biochip. Although the zone of fluid active in the reactions with the biochip is only a few micrometers in depth from the surface of the biochip, because of the large volume of liquid used to immerse the biochip, relatively large amounts of energy are needed for the heating and agitation steps. Furthermore, due to the open-topped nature of the containers, the biochip is susceptible to contamination and, when infectious samples are used, these can prove hazardous to the health of the user. This is particularly a problem if vapor is released through heating and agitation. As an alternative to fluid baths, biochip wells may be used to house the biochip in assay protocols, see for example US2013/0224878. However, these also require relatively large volumes of fluid, and so do not overcome the above-mentioned problems.

It would therefore be beneficial to reduce the risk of biochip contamination and health risks to the user when infectious samples are used.

Some examples of known analysers are found in U.S. Pat. No. 6,399,394, WO 02/072264 and US 2005/0047973.

In accordance with an aspect of the invention, there is provided a fluidic card assembly comprising a fluidic card housing and a biochip located in the fluidic card housing, wherein the fluidic card housing includes a chamber with a base wall, into which at least one fluidic channel extends, the biochip being at least partially located in the chamber, and a seal for sealing the biochip in the chamber when the biochip is urged into the chamber, and wherein the fluidic channel has a serpentine form.

The invention provides a fluidic card assembly having a chamber that is configured to provide a recess for integration of a biochip. Once the biochip is fully urged into the chamber, the biochip is sealed in its fully urged position by the seal such that a small amount of fluid may be delivered in a controlled way from the at least one fluidic channel across the surface of the biochip, without risk of leakage. Thus the biochip itself is used as part of the leak proof seal.

The design means that the fluid is dropped directly from the channel on to the surface of the biochip.

Preferably the seal has a shore hardness of A20-50. The shore hardness is measured according to ISO868 methods. The measurement is taken using the following protocol: The shore hardness of the material of the seal is measured using a durometer. The Shore A durometer has a hardened steel rod indenter 1.1 mm-1.4 mm diameter with a truncated cone angled 35° from the axial plane of the rod closing to a 0.79 mm diameter at the tip. A 0.822 kg mass is applied to the material for a duration of 15 s, then the depth of any indent is measured. A hardness Shore A100 is given for an indent of 0 mm and a hardness Shore A0 is given for an indent of 2.54 mm. The seal may be made from any material known to the person skilled in the art, though in a particularly preferred embodiment, the seal is made from TPE or silicone materials.

The great advantage of this structure is that only small volumes of liquid are needed. The liquid is transported through the at least one fluidic channel and across the surface of the biochip when it is urged into the chamber. Heating the small volume of liquid requires little energy and is more efficient since the biochip is in an isolated chamber where the vapour cannot escape into the atmosphere. Any pressure increase in the biochip chamber increases the temperature of the biochip further. Agitation is not required, as the exposure of the biochip to the fluid is by a flow rate across the surface of the biochip, thus providing an additional advantage over conventional fluid baths.

The design allows the biochip to be easily removed or swapped if required. The biochip does not have to be permanently fixed within the fluidic card assembly.

The fluidic channel has a serpentine form providing uniform flow with turbulence at the bends. This causes increased mixing so that the biochip is exposed to more target in a sample, leading to a faster reaction.

In a preferred embodiment, the fluidic card assembly is a microfluidic card assembly, wherein the at least one fluidic channel is a microfluidic channel. "Microfluidic channel" is defined as a channel that transports only microlitres of liquid rather than millilitres of fluid. Thus in this preferred embodiment, only a few microlitres of fluid is required, preferably 1-50 microlitres, more preferably 5-30 microlitres to run the assay(s) on the biochip. This can potentially save up to hundreds of litres of liquid per year for a laboratory.

Because the biochip is a separate element and it is urged into the fluidic card assembly prior to use, materials can be present on the biochip that are compatible with different antigens/antibodies but not compatible with fluidic card assembly manufacture. This gives great flexibility in the type of biochip that can be used in the fluidic card assembly, and allows biochip design to be enhanced and developed further without the restriction of needing to be compatible with fluidic card manufacture. The biochip can be selected according to the assay/test to be performed and any biochip can be used provided that it fits within the recess of the chamber. A biochip may be selected that gives better control of background signal that would otherwise influence a result. For example, a ceramic biochip gives less background signal, such that light is only detected from reaction zone spots on the biochip leading to a more accurate test result. Preferably the biochip is a ceramic biochip. In some cases a transparent biochip may be used.

The housing may be made of any suitable material. In a preferred embodiment, the housing is made of plastic or other polymers, preferably plastic. In a particularly preferred embodiment, the plastic housing consists of polypropylene.

Combining plastics and ceramics means that the thermal properties of the materials can be mixed and matched resulting in a fluidic card assembly having tailored thermal properties. If desired, heat can be directed to specific areas of the fluidic card assembly using thermal boundaries formed by contiguous materials having different thermal conductivities.

The at least one fluidic channel may be partially embedded within the fluidic card housing such that the at least one fluidic channel is open-sided. In this embodiment, a cover is applied to the fluidic card housing to close the at least one fluidic channel to prevent liquid leaking from the fluidic card assembly. The cover may partially cover the fluidic card housing providing that it covers all of the open-sided fluidic channels in the fluidic card housing in order to make them closed vessels. If there are any omitted portions of the housing, such as a viewing window in the biochip chamber region, these must also be covered by a cover, preferably the same cover used to close the open-sided fluidic channels.

The cover may be made of any suitable material known to the person skilled in the art. In a preferred embodiment, a plastic film may be used. In a preferred embodiment, a transparent cover is used. In a particularly preferred embodiment, a polypropylene film is used. The cover may be attached by any means known to the person skilled in the art. For example, the cover may be laser welded to the fluidic card housing. The cover may extend to cover the whole of the surface of the fluidic card housing. Alternatively, the cover may partially cover the fluidic card housing provided that it covers all of the open-sided fluidic channels in the fluidic card housing in order to make them closed vessels, and if there are any other omitted portions of the housing; the cover should also cover these. Preferably, the cover extends across the whole of the surface of the fluidic card housing.

In a preferred embodiment, fluids can also be removed from the biochip surface by means of a second fluidic channel. Therefore, preferably the at least one channel includes an inlet fluidic channel and an outlet fluidic channel. The advantage of having an inlet channel and an outlet channel is that a controlled movement of fluid is provided on to and off the biochip surface. There may be more than one inlet channel and more than one outlet channel.

The fluidic card housing may further comprise a fluid inlet port and a fluid outlet port. The advantage of this is to facilitate the controlled movement of fluids into the inlet fluidic channel and out of the outlet fluidic channel. Multiple fluid inlet ports and multiple fluid outlet ports may be provided in the fluidic card housing. However, in a preferred embodiment, there is provided a single fluid inlet port and a single fluid outlet port.

The fluidic card assembly may comprise a valve system for controlling the movement of fluids in and out of the assembly and through the at least one fluidic channel. The valve is used to either regulate the flow rate of fluids or to stop the flow of fluids by blocking the flow channel. The valve can be opened, or unlocked, to allow fluid into the system, and can then be closed, or locked, to lock fluid within the chamber. The valve can therefore provide a perfectly closed system, free from risk of contamination, infection, and leakage.

The valve system can be opened and closed to selectively connect the at least one fluidic channels. In this manner, the valve system controls whether the fluidic channel(s) are open and closed in any arrangement.

Various valve technologies known to the skilled person can be used. The valve can either be integrated on the fluidic card, or the valve system can be off-card. In a preferred embodiment, a membrane valve is integrated on the card.

The design of the fluidic card assembly allows a 'floating' biochip configuration wherein the biochip is located in the chamber but not fully urged into the chamber. Whilst in this floating configuration, there is no seal formed between the biochip and the seal. While the biochip is floating, there is negligible force acting on the surface of the biochip, protecting the surface treatment from damage that may otherwise occur due to stresses involved in clamping the biochip against a surface over a prolonged period of time. By floating the biochip in the biochip chamber, the biochip is more resistant against damage by sudden 'shock' impact forces as the impulse force of any impact is reduced. The biochip can also be removed from the biochip chamber and thus from the fluidic card assembly at any time for any reason while in its floating state.

A flexible membrane may be adhered over the biochip to retain the biochip at least partially in the chamber and in the sealing condition. This has a great advantage that the biochip can be held in place by a removable membrane such that the biochip is not a permanent fixture within the fluidic card assembly. The membrane can be removed in order to access and/or remove the biochip. The biochip can be removed from the housing and stored for future processing. Additionally, it is possible that the fluidic card assembly can be cleaned and used again for holding a different biochip. The flexible membrane may be any material that can retain the biochip when it is at least partially inserted into the chamber, and any material type compatible with the assay. In a preferred embodiment, the flexible membrane is made of polypropylene. The flexible membrane may comprise a thermally conductive material in order to provide a thermal interface to heat the biochip. A thermally conductive flexible membrane improves the flow and spread of heat to the biochip, providing improved conditions for biochemical reactions on the biochip. A window portion can be provided in the flexible membrane, for example in the form of a transparent section of the flexible membrane or use of a completely transparent flexible membrane. This provides a line of sight to the biochip placed within the chamber. This helps with acquiring data, and with manufacturing quality control in regard to placing the ceramic layer in the correct orientation.

A clamp may be used to retain the biochip at least partially in the chamber and/or retain the biochip in its fully engaged position after the biochip has been fully urged into the chamber. It is possible that the membrane be used to retain the biochip at least partially in the chamber and then use a clamp to urge the biochip into the fully urged position.

In a preferred embodiment, the flexible membrane adhered over the biochip urges the biochip into the chamber and retains the biochip in its fully urged position. This has the advantage that no clamp is required to form a seal between the seal and the biochip. The fluidic card assembly having a fully urged biochip can be inserted into the biochip analyser without any further urging of the biochip into the chamber.

The flexible membrane can be adhered to any part of the fluidic card assembly that allows the biochip to be securely held in the desired position and that prevents leakage of fluid from the biochip chamber. The flexible membrane may be secured to a portion of the fluidic card housing wherein the portion of the housing surrounds the entire biochip chamber. In a preferred embodiment, the flexible membrane may be secured to a portion of the fluidic card housing and secured to part or all of the biochip itself.

The flexible membrane may be adhered by any suitable means known to the skilled person. For example, the membrane may be laser welded or attached via an adhesive that allows the membrane to be removed after use of the fluidic card, Removal of the flexible membrane allows access and/or removal of the biochip from the biochip chamber. A knife or other implement may be used to cut through the membrane or to lever the membrane away from the fluidic card housing and biochip, with relatively little force. In a preferred embodiment, an optimised laser weld is used to allow the flexible membrane to be peeled by hand with relatively little force. Alternatively, an induction seal, heat seal or an adhesive can be used to connect the flexible membrane to the fluidic card housing and biochip to allow peeling of the membrane by hand. Preferably an adhesive is used. Alternatively, and more preferably, a heat seal is used.

The fluidic card assembly may optionally comprise a member for guiding the biochip into the chamber. The guide member may act to prevent movement of the biochip from side to side when the biochip is partially inserted into the chamber and before it has been fully urged and sealed into the chamber.

The biochip chamber may be configured to allow different detection methods to be used. Suitable detection methods are chosen according to the type of assay run on the biochip and the detection method required to analyse the assay.

In a preferred embodiment, chemiluminescence is used as the detection method and so a clear line of sight is provided to view the biochip. This may be achieved wherein at least a portion of the base wall of the biochip chamber is omitted and wherein a corresponding portion of the seal is omitted, to provide a viewing window through which at least a portion of the biochip can be viewed. The shape and dimension of the portion omitted from the base wall of the biochip chamber and seal can be varied according to the biochip used. The portion omitted from the base wall of the biochip chamber and seal may be of appropriate size to allow the entire reactive surface of the biochip to be viewed. The number of tests that can be performed is greatest when the entire reactive surface of the biochip is viewed.

In a particularly preferred embodiment, multiple portions of the base wall of the biochip chamber are omitted and the corresponding portions of the seal are omitted, to provide a patterned viewing window through which portions of the biochip can be viewed. The portions omitted from the biochip chamber base wall and seal form a pathway that precisely directs fluid over the surface of the biochip. The pathway reduces the area of the biochip available for tests. However, the pathway better controls fluid and better removes any bubbles and/or foam that may be present on the biochip surface.

In the manufacture of biochips, it is easier to spot the biochip with reaction zones in straight rows, Therefore, in an even further preferred embodiment, the viewing window comprises a series of parallel lines. The rows of biochip reaction zone spots are viewed through the viewing window. The window and parts of the fluidic card housing may cooperate to define a serpentine fluidic path. The serpentine shape is etched into the base wall of the biochip chamber. When the biochip is sealed into the biochip chamber, the fluid is directed across the portions of biochip visible to the user in a serpentine fashion. The advantage of this serpentine embodiment is that the serpentine configuration acts as a blinker, such that any material on the biochip, other the reaction zone spots, that emits light is shielded from view such that it does not confuse the result, A more accurate result is obtained.

The portion(s) omitted from the biochip chamber base wall and seal may be chosen according to the biochip type, number of spots and the properties of the fluids introduced into the fluidic channels and across the biochip surface.

Irrespective of the shape and/or size of the viewing window formed from the omitted portion(s) of the base wall of the biochip chamber and the corresponding portion(s) of the seal, a transparent cover is applied to the fluidic card housing in order to cover at least the viewing window to prevent leaking of liquid from the biochip chamber and also to prevent contamination of the biochip. Where the at least one fluidic channel is partially embedded within the fluidic card housing such that the at least one fluidic channel is open-sided, the cover applied to the viewing window fluidic card may also cover the at least one fluidic channel to prevent liquid leaking from the fluidic card assembly.

In a preferred embodiment, there is a window provided in the flexible membrane and also in the base wall and corresponding portion of the seal, so that there is visual line of sight to the topside and underside of the biochip.

Preferably, the transparent cover applied to the fluidic card housing is a transparent film. The advantage of this is that the total width of the fluidic card assembly is relatively thin, and less bulky to handle, requiring less room for storage. In a preferred embodiment, the total thickness of the fluidic card assembly is approximately 0.5-2 mm thick, more preferably 1 mm thick.

If the assay is detected via other methods, such as electrochemical detection, a viewing window may not be necessary and different detection features may be provided. In the case of electrochemical detection, the fluidic card assembly may comprise electrodes within the chamber. Therefore, space may be allocated for electrodes within the chamber.

In another aspect of the invention, a fluidic card housing is provided wherein the housing includes a chamber with a base wall, into which at least one fluidic channel extends, and a seal for sealing a biochip in the chamber when the biochip is urged into the chamber. The fluidic card housing is provided for use in an assembly according to any embodiment described above.

In yet a further aspect of the invention there is provided a method of analysing a biochip wherein mounting a fluidic card assembly, according to any embodiment described above, to a fluidic card analyser allows signal data to be collected from the biochip, processed, and turned into a test result. The biochip analyser is constructed in such a way that accommodates a fluidic card assembly according to the present invention, preferably wherein the biochip is already urged into the chamber against the seal. Alternatively, the biochip analyser may cause the urging of the biochip into the biochip chamber. Because the biochip is a separate element and is urged into the fluidic card assembly prior to use, materials can be present on the biochip that are not compatible with fluidic card assembly manufacture, giving great flexibility in the type of biochip that can be used in the fluidic card assembly.

In yet a further embodiment of the invention, there is provided a method of analysing a biochip wherein mounting a fluidic card assembly, according to any embodiment described above, to a fluidic card analyser causes the biochip to be urged into the chamber against the seal. The fluidic card assembly is built to accommodate a particular assay, though the assay process is developed to be generic for a large number of tests. The fluidic card analyser is built around the fluidic card assembly and so provides all of the interfacing modules required to complete an assay on the fluidic card assembly, Generally an analyser will only be compatible with a fluidic card assembly that has complementary interfaces for completing an assay. Usually this means an analyser will only be compatible with a single fluidic card assembly design, though the design of the fluidic card assembly may be such that it can run any number of different tests.

In the invention, a "Biochip" is a general term for a reaction platform having at least one reaction zone to detect specific biomarker(s) or analyte(s). Biochips generally comprise a substrate, such as silicon, ceramic or glass. In a preferred embodiment, a ceramic biochip is used. In a particularly preferred embodiment, a Randox 9×9 mm ceramic slide may be used. Some biochips carry a very large number of such reaction zones, making it possible to carry out a large number of assays simultaneously, and using the same single sample for each assay. A variety of biochips are available from Randox Laboratories Limited, such as Cardiac Arrays, Drugs of Abuse Arrays, Fertility Hormone Arrays and Tumour Monitoring Arrays. These have multiple reaction zones designed to perform a series of tests relating to the specific condition intended to be diagnosed. The specific biochip is chosen according to the assay to be performed and in order to get the best signal and the most accurate assay results.

Embodiments of the invention are described in detail below with reference to the accompanying figures, in which.

Figure 1:
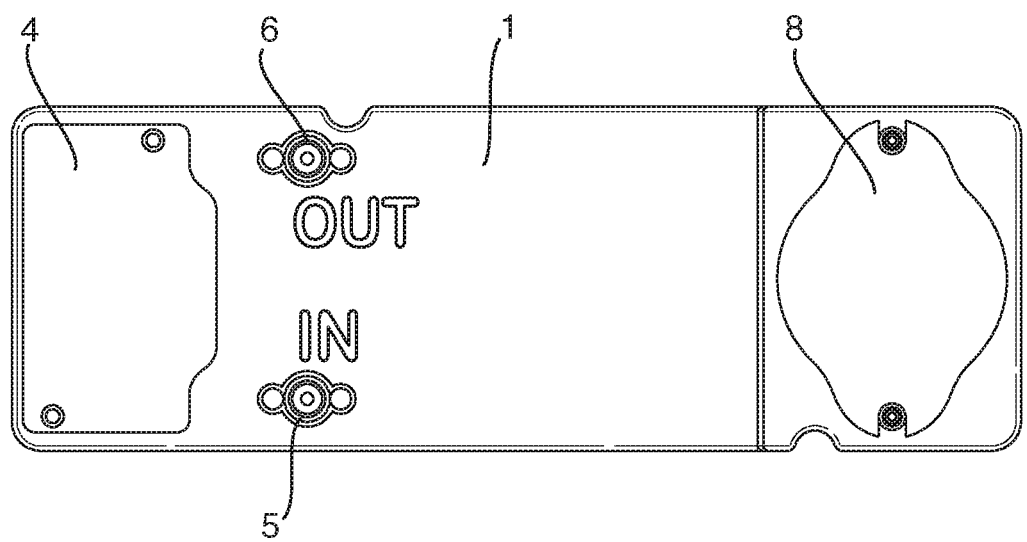
FIG. 1 shows the underside of a fluidic card assembly of a first embodiment of the invention.
Figure 2:
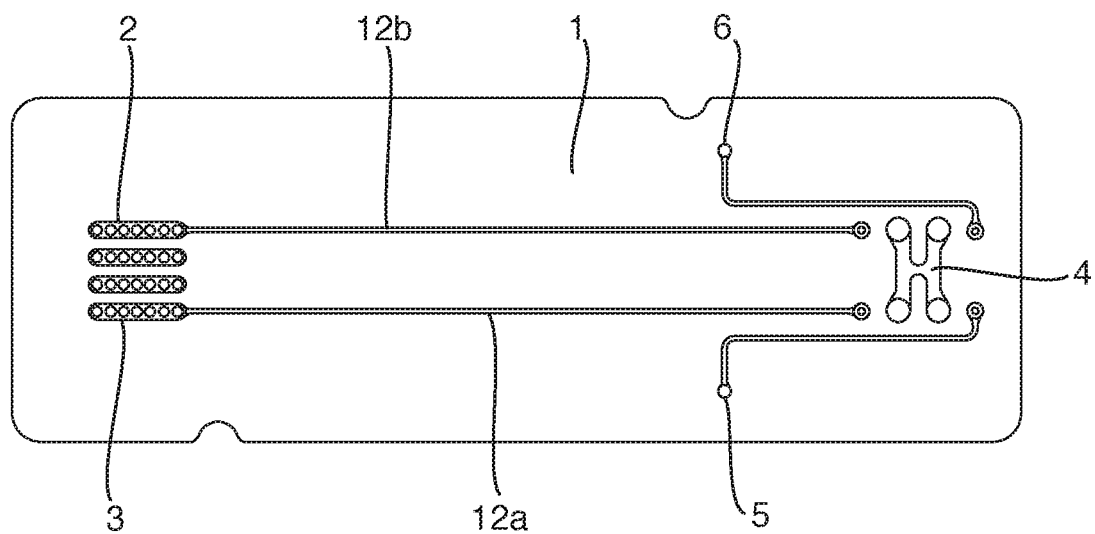
FIG. 2 shows the topside of the first embodiment of the fluidic card assembly when fully assembled.
Figure 3:
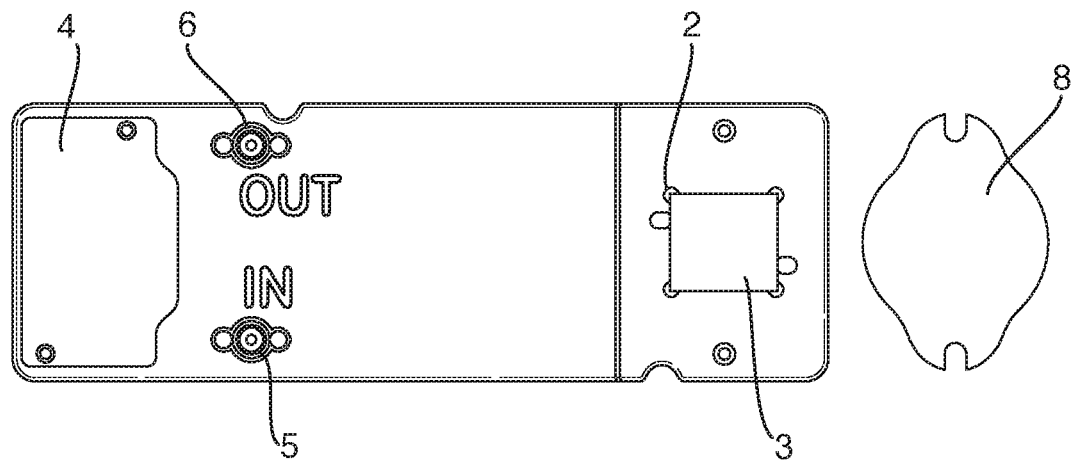
FIG. 3 shows the underside of the first embodiment of the fluidic card assembly, with biochip exposed.
Figure 4:
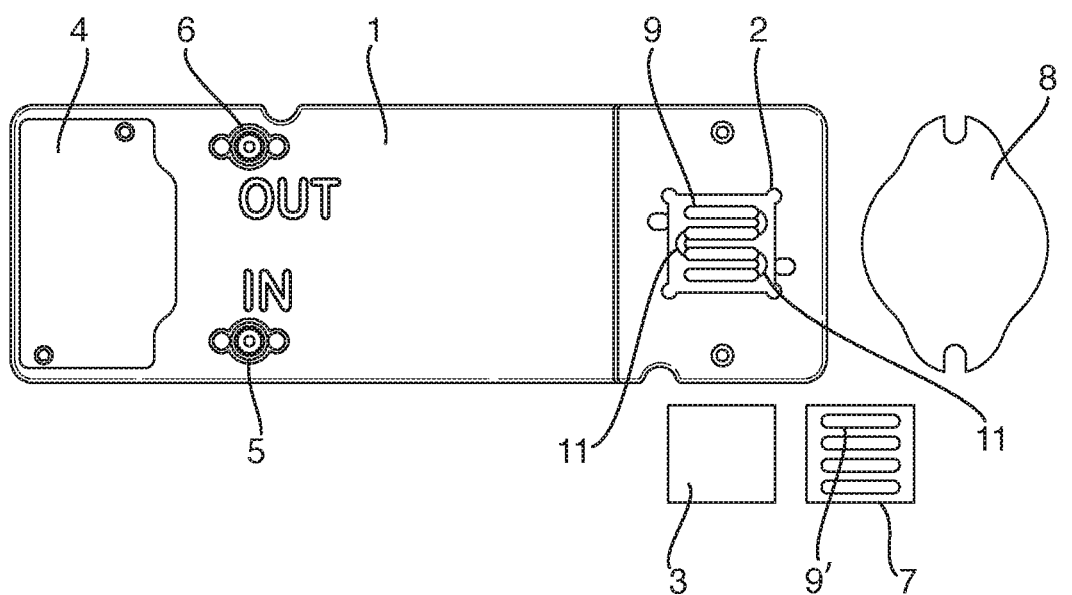
FIG. 4 shows the underside constituent parts of the first embodiment of the fluidic card assembly.
Figure 5:
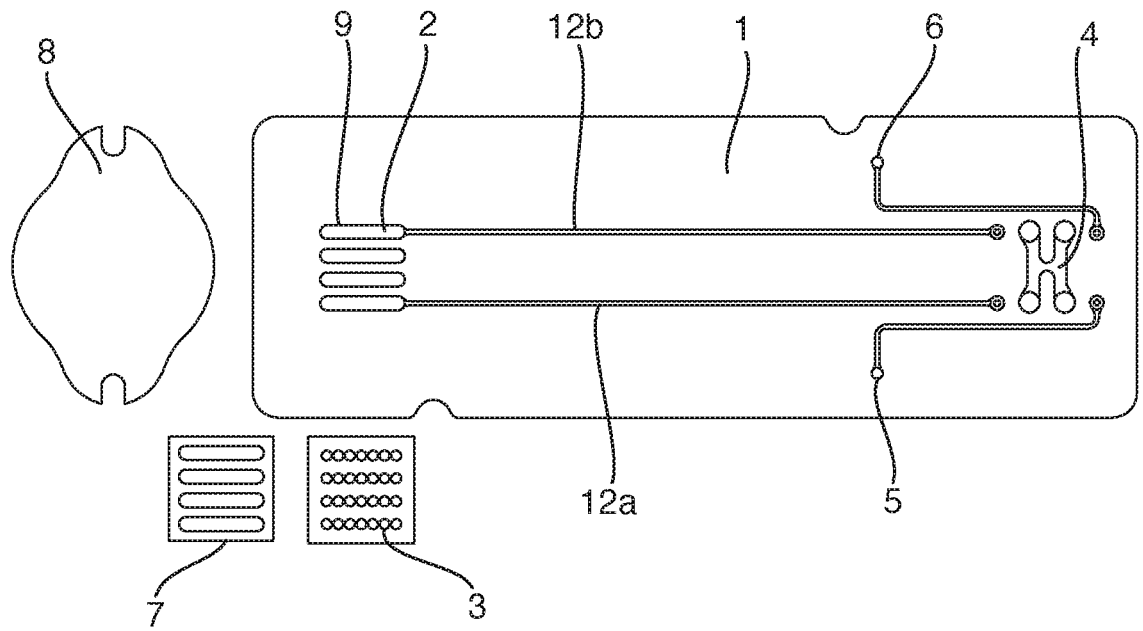
FIG. 5 shows the topside constituent parts of the first embodiment of the fluidic card assembly.

As shown in FIGS. 1 to 5, the first embodiment of the fluidic card assembly comprises a fluidic card housing 1 formed as a plastics moulding. The plastic is unreactive with the fluids introduced into the fluidic card assembly. The fluidic card housing 1 can be clamped to an analyser (not shown). The fluidic card housing includes a biochip chamber 2 having a base wall (not visible), into which microfluidic channels, 12*a*, 12*b*, extend. The microfluidic channels, 12*a*, 12*b* are partially embedded within the fluidic card housing 1 such that the microfluidic channels are open-sided. A cover in the form of a transparent film (not shown) is applied to the whole surface of the topside of the fluidic card assembly to close the microfluidic channels 12*a*, 12*b*, in order to prevent liquid leaking from the fluidic card assembly.

A polymer seal 7 (FIG. 4), is located within the biochip chamber and sits flush against the base wall of the biochip chamber.

A biochip 3 is located within the biochip chamber 2, the shape and size of the chamber being approximately the same as the biochip 3. The biochip chamber is selected to conform to the shape of the biochip and is typically square. The biochip is placed into the biochip chamber on top of the seal and such that the reactive surface is positioned facing towards the base wall of the biochip chamber. The biochip is at least partially inserted into the biochip chamber. Typically, the biochip chamber has a width of 9.1 mm, a length of 9.1 mm, and a depth of 0.5 mm in order to accommodate the biochip. Typically the volume of the biochip is 41 µl.

A flexible membrane 8 is adhered over the biochip to retain the biochip 3 in the biochip chamber 2. The flexible membrane is attached to the underside of the fluidic card housing 1, by welding and optionally may also be attached to the biochip itself. The flexible membrane is made of any suitable material that can retain the biochip in the chamber in its fully urged position, so as to form a seal between the biochip and the seal. Preferably the membrane is peelable such that it can be peeled away from the housing and/or biochip by hand with relatively little force, thus allowing the biochip to be removed.

A membrane valve system 4 is provided to control the movement of fluids in and out of the fluidic card assembly. The valve system can be opened or unlocked, to allow fluid into the system, and can then be closed or locked, to lock fluid within the chamber. The valve is able to provide a perfectly closed system, free from risk of contamination, leakage and infection.

A fluid inlet port 5 is provided, through which liquids can be introduced into the microfluidic inlet fluidic channel 12*a* found in the fluidic card housing. The fluid inlet port allows liquids to be introduced by syringe pumps, pipettes or other devices that are able to hold and expel liquids or to feed liquids to a particular location. A fluid outlet port 6 is also provided. This allows liquids to be removed or expelled from the microfluidic outlet fluidic channel 12*b*.

According to the first embodiment of the fluidic card assembly, multiple portions of the base wall of the biochip chamber 9 are omitted and corresponding portions 9' of the seal are omitted, to provide a patterned viewing window (in this case a series of parallel lines) through which portions of the biochip 3 can be viewed through the topside of the fluidic card housing 1. In this embodiment, a serpentine fluid path configuration is formed by etching a communicating pathway 11 (FIG. 4) into the base wall of the biochip chamber to connect the series of parallel lines to form a serpentine pathway. When the biochip is sealed in the chamber it allows the fluid to be directed across the omitted portions so that fluid moves across the portions of biochip visible to the user in a serpentine fashion. Preferably, the serpentine configuration is 0.5 mm deep on the straights and 0.25 mm deep on the curved corners. Preferably, the track covers an area 43 mm$^2$ and has a volume of 20 µl.

Instead of a serpentine fluid path configuration, it is of course possible to have an alternative pattern of omitted sections and thus have a different shaped/patterned window to the surface of the biochip. It is also possible to have a single omitted section to form a single viewing window.

The microfluidic card may be supplied without a biochip in the chamber. The user may choose a biochip depending on the assay to be run, and insert it into the biochip chamber 2 on top of the seal 7 and such that the reactive surface is positioned facing towards the base wall of the biochip chamber 2. Next the user can place a flexible membrane 8 over the biochip 3 and secure the flexible membrane 8 over the biochip 3 to secure the biochip in place at least partially in the chamber 2. In a preferred embodiment, the user places the flexible membrane 8 over the biochip 3 and at least a part of the housing 1 such that the biochip 3 is urged into the biochip chamber 2 to its sealing position. After use, the flexible membrane 8 may be removed by using an implement, such as a knife, using relatively little force or by hand, allowing the biochip 3 to be removed and so that the card housing can be reused with another biochip. Preferably the flexible membrane is removed by hand.

Figure 6:
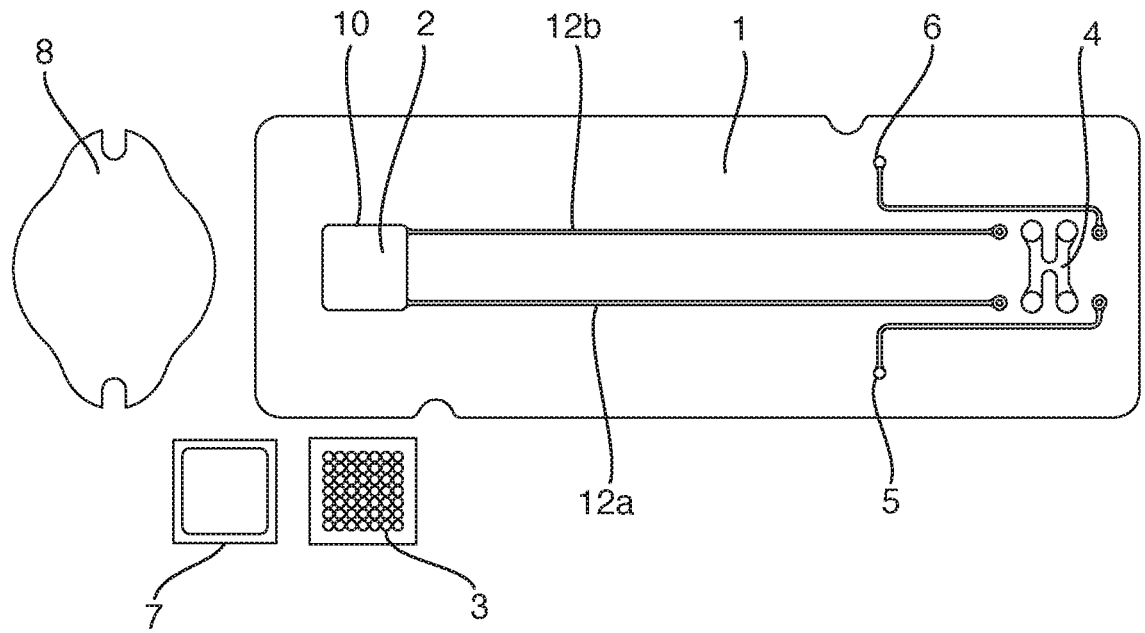
FIG. 6 shows the topside constituent parts of a fluidic card assembly of a second embodiment of the invention.
Figure 7:
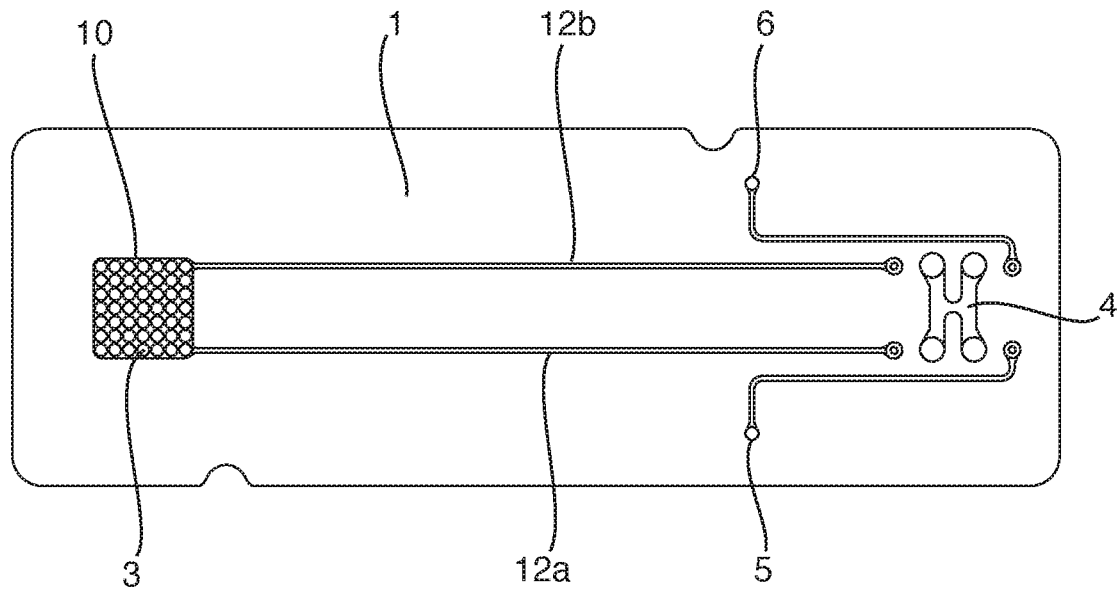
FIG. 7 shows the topside of the second embodiment of the fluidic card assembly when fully assembled.

FIGS. 6 and 7 show the topside of a fluidic card assembly of a second embodiment of the invention. As can be seen from these figures, a large portion of the base wall of the biochip chamber is omitted 10 and a corresponding portion of the seal is omitted 7, such that a viewing window is provided that allows the entire reactive surface of the biochip to be seen 3, when the biochip is located in the biochip chamber. The flange of the biochip 3 is retained within the biochip chamber 2 so that the biochip 3 cannot fall out of the biochip chamber. The number of tests that can be performed is greatest when the entire reactive surface of the biochip can be seen. A cover in the form of a transparent film (not shown) is applied to the whole surface of the topside of the fluidic card assembly to prevent leakage of fluid from the fluidic card assembly and to prevent contamination of the biochip.

Figure 8:
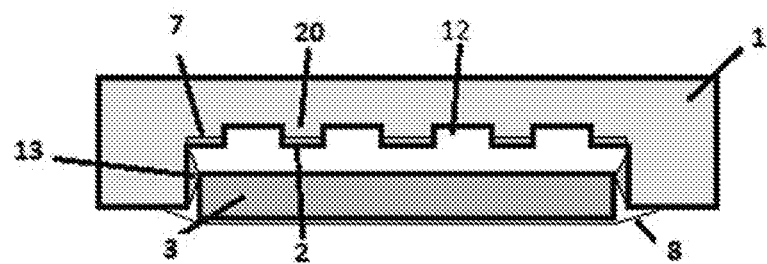
FIG. 8 shows a cross-section through the biochip chamber of a fluidic card assembly of the third embodiment of the fluidic card assembly, wherein the biochip is partially located in the chamber and retained by a flexible membrane.

FIG. 8 shows a cross section of the fluidic card assembly according to a first embodiment of the invention before the biochip is fully inserted into the sealing position. Four microfluidic channels 12 extend into the base wall 20 of the biochip chamber 2. The biochip 3 is at least partially located in the biochip chamber 2. The seal 7 is present in the biochip chamber to form a seal between the biochip and the seal. An optional guide member 13 is present to prevent movement of the biochip from side to side whilst it is partially inserted in the chamber but before it is fully urged into the chamber. A peelable flexible membrane 8 is secured over the biochip to retain the biochip in the chamber. "Peelable" means that the user is able to peel the membrane by hand.

Figure 9:
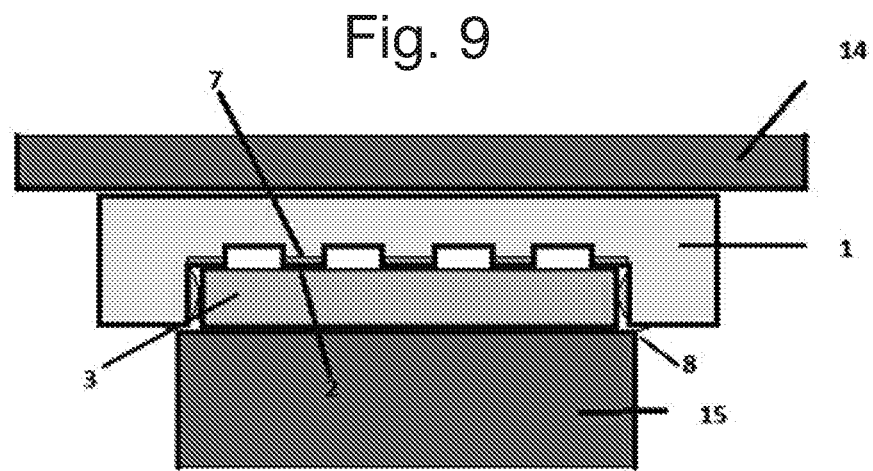
FIG. 9 shows a cross-section through the biochip chamber of a fluidic card assembly of a third embodiment of the fluidic card assembly, wherein the biochip is fully urged into the chamber by two clamps, and wherein the biochip is sealed in the chamber.

FIG. 9 shows the fluidic card assembly according to a first embodiment of the invention, wherein the biochip 3 is urged into the biochip chamber 2 by two clamps 14, 15 either side of the fluidic card housing 1, thereby forming a seal between the seal 7 and the biochip. In this embodiment, the flexible membrane 8 does not necessarily provide the sufficient force to urge the biochip into the chamber. However, the flexible membrane at least partially retains the biochip within the biochip chamber and also prevents leakage of liquids form the chamber 2.

Figure 10:
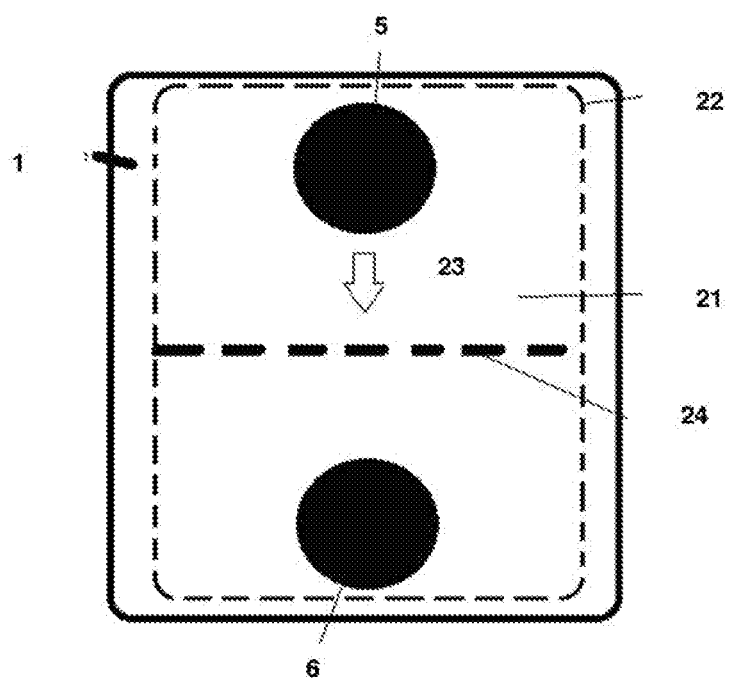
FIG. 10 shows the membrane valve of the first and second embodiment of the fluidic card assembly.

FIG. 10 shows a membrane valve according to embodiments 1 or 2 of the invention. A membrane valve in this instance consists of a flexible film 21, such as a flexible foil, covering the rigid surface of the fluidic card housing 1 on which the at least one fluid inlet port 5 and at least one fluid outlet port 6 are present. The flexible film 21 is bonded to the fluidic card housing 1 around the fluid inlet and fluid outlet ports but not in the space between the ports, preferably via a flexible foil seal 22. Fluid 23 can thus move freely between the inlet and outlet ports with the flexible film in place and the membrane valve is 'open'. The membrane valve is 'closed' by pressing a rigid actuator against the film at a rigid actuator interface 24, thereby pushing the film on to the rigid surface of the fluidic card housing along the area where the film is not bonded to the surface. When the film is pushed in contact with the surface between the inlet and outlet ports fluid flow 23 between the ports is inhibited.

In another aspect of the invention, a biochip analyser is provided that can be used in conjunction with a fluidic card assembly according to the present invention. The biochip analyser is adapted such that a fluidic card assembly according to the present invention can be mounted to it allowing signal data from the biochip to be collected, processed and interpreted into a result for whichever assay(s) is/are performed on the biochip. The biochip analyser is constructed in such a way that accommodates a fluidic card assembly according to the present invention, preferably wherein the biochip is already urged into the chamber against the seal. Alternatively, the biochip analyser may accommodate a fluidic card assembly having a biochip in its floating configuration, wherein mounting of the fluidic card assembly causes the urging of the biochip into the biochip chamber.

Figure 11:
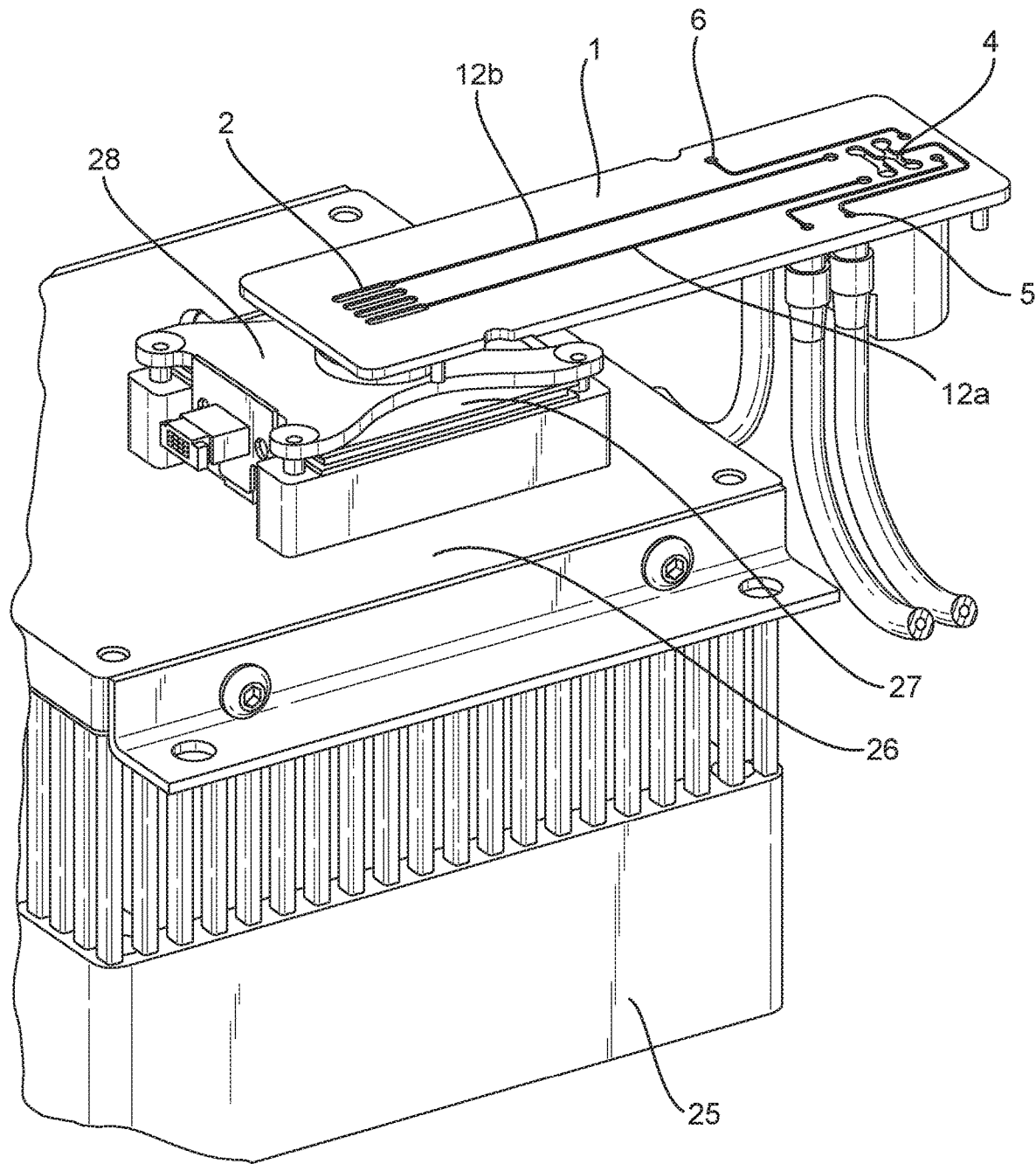
FIG. 11 shows the interface between a fluidic card assembly according to one aspect of the invention when engaged with a fluidic card assembly according to another aspect of the invention.

FIG. 11 shows a biochip analyser according to the present invention. The analyser comprises a fan 25, a heat sink 26 and a heater 27. A heat spreader clamp 28 is provided on top of the heater, onto which the fluidic card housing 1 can be mounted.

The card technology can be employed as part of a larger card, which includes on-board reagents and sample preparation. In one embodiment, on-board reagents can be stored on-card inside wells purposefully integrated in to the material of the fluidic card housing. In another embodiment, on-board reagents can be housed in frangible blister packs that are joined to the fluidic card housing where reagents are released in to the card by bursting the blister pack. Sample preparation can be implemented by adding further layers and/or wells to the card layout to allow for transport of fluids along a set path in the card, where the fluids are subjected to processing at various times according to an assay procedure. In this case, it is possible to add reagents to the housing during the manufacturing process, for example by putting dried reagent on at least one wall of a fluidic channel or microfluidic channel.

The fluidic card assembly of the present invention may be provided with a biochip pre-fitted in the biochip chamber in its floating configuration. The user has the option to remove the biochip after processing on the fluidic card assembly either for reference or for further processing.

In another aspect of the invention, a kit of parts is provided, wherein the kit comprises i) a microfluidic card having an empty biochip chamber and ii) a biochip for insertion into the biochip chamber by the user.

The invention claimed is:

1. A fluidic card assembly comprising a fluidic card housing having a topside and an underside and a biochip located in the fluidic card housing, wherein the fluidic card housing includes a chamber with a base wall, into which at least one fluidic channel extends, the biochip being at least partially located in the chamber, and a seal for sealing the biochip in the chamber when the biochip is urged into the chamber, and wherein the fluidic channel has a serpentine form;

the fluidic card assembly further comprises a flexible membrane on the underside of the fluidic card housing adhered over the biochip to retain the biochip at least partially in the chamber in a 'floating' biochip configuration when the biochip is located but not fully urged in the chamber, and the fluidic card assembly further comprises a guide member to prevent side to side movement of the biochip while the biochip is at least partially located in the chamber, and wherein when the biochip is in a floating configuration there is no seal formed between the biochip and the seal, and wherein when the biochip is fully urged into the chamber, the biochip is sealed in its fully urged position to the seal.

2. The fluidic card assembly according to claim 1, wherein the at least one fluidic channel is a microfluidic channel.

3. The fluidic card assembly according to claim 1, wherein the at least one fluidic channel is partially embedded within the fluidic card housing such that the at least one fluidic channel is open-sided, and wherein a cover is applied to the fluidic card housing to close the at least one fluidic channel to prevent liquid leaking from the fluidic card assembly.

4. The fluidic card assembly according to claim 1, wherein the at least one channel includes an inlet fluid channel and an outlet fluid channel.

5. The fluidic card assembly according to claim 1, wherein the fluidic card housing further comprising a fluid inlet port and a fluid outlet port.

6. The fluidic card assembly according to claim 1, wherein the assembly further comprises a valve system for controlling the movement of fluids in and out of the assembly and through the at least one fluidic channel.

7. The fluidic card assembly according to claim 6 wherein the valve system can be opened and closed to selectively connect the at least one fluidic channels.

8. The fluidic card assembly according to claim 1, wherein the membrane is secured to the underside of the fluidic card housing and over the biochip by laser welding; induction seal; heat seal or adhesive, preferably wherein the user is able to peel the membrane by hand.

9. The fluidic card assembly according to claim 1, wherein the membrane is secured to the underside of the fluidic card housing surrounding the biochip and optionally at least a portion of the biochip.

10. The fluidic card assembly according claim 1, wherein at least a portion of the base wall of the biochip chamber is omitted and a corresponding portion of the seal is omitted, to provide a viewing window through which at least a portion of the biochip can be viewed.

11. The fluidic card assembly according to claim 10, wherein multiple portions of the base wall of the biochip chamber are omitted and corresponding portions of the seal are omitted, to provide a patterned viewing window through which portions of the biochip can be viewed, preferably wherein the viewing window comprises a series of parallel lines.

12. The fluidic card assembly according to claim 10, wherein the window and parts of the fluidic card housing cooperate to define a serpentine fluidic path.

13. The fluidic card assembly according to claim 10, wherein a cover is applied to the fluidic card housing to cover the omitted portion(s) of the chamber wall to prevent the leaking of liquids from the fluidic card housing and contamination of the biochip.

14. The fluidic card assembly according to claim 3, wherein the cover is a transparent film.

15. The fluidic card assembly according to claim 1, further comprising electrodes within the chamber.

16. A method of analysing a biochip, the method comprising;

mounting the fluidic card assembly according to claim 1 to a fluidic card analyser causing the biochip to be urged into the chamber against the seal;

collecting signal data from the biochip; and processing the data to obtain a test result.

17. A fluidic card analyser constructed in such a way that when a fluidic card assembly according claim 1 is mounted against the biochip analyser, the biochip is urged into the chamber against the seal and signal data can be collected from the biochip, processed, and turned into a test result.

* * * * *